United States Patent [19]

Kamei et al.

[11] Patent Number: 5,716,640
[45] Date of Patent: Feb. 10, 1998

[54] METHOD OF PRODUCING SUSTAINED-RELEASE MICROCAPSULES

[75] Inventors: Shigeru Kamei, Takarazuka; Minoru Yamada, Kawanishi; Yasuaki Ogawa, Ohyamazaki-cho, all of Japan

[73] Assignee: Takeda Chemical Industries, Ltd., Osaka, Japan

[21] Appl. No.: 705,348

[22] Filed: Aug. 29, 1996

Related U.S. Application Data

[62] Division of Ser. No. 562,634, Nov. 27, 1995, Pat. No. 5,575,987, which is a continuation of Ser. No. 115,149, Sep. 2, 1993, abandoned.

[30] Foreign Application Priority Data

Sep. 2, 1992 [JP] Japan ..................... 4-234821

[51] Int. Cl.$^6$ ............... A61K 9/48; A61K 9/14; A61K 9/50; B32B 5/16
[52] U.S. Cl. ............ 424/451; 424/489; 424/501; 424/502; 514/963; 264/4.1; 264/4.3; 264/4.33; 264/4.7; 428/402; 428/402.2; 428/402.21
[58] Field of Search ............ 264/4.1, 4.3, 4.33, 264/4.7; 424/451, 489, 501, 502; 428/402.2, 402.21

[56] References Cited

U.S. PATENT DOCUMENTS 3,956,172  5/1976  Saeki et al. ................. 252/316

FOREIGN PATENT DOCUMENTS

| | | |
|---|---|---|
| 0 145 240 | 6/1985 | European Pat. Off. |
| 0 178 824 | 4/1986 | European Pat. Off. |
| 0 442 671 | 8/1991 | European Pat. Off. |
| 4 217 914 | 5/1990 | Japan. |
| 2 246 514 | 2/1992 | United Kingdom. |
| 8 904 673 | 6/1989 | WIPO. |

*Primary Examiner*—Carlos A. Azpuru
*Attorney, Agent, or Firm*—Foley & Lardner

[57] ABSTRACT

A method of producing sustained-release microcapsules containing a biologically active substance from an W/O emulsion comprising an inner aqueous phase containing said biologically active substance and an external oil phase containing a biodegradable polymer, characterized in that microcapsules formed on microencapsulation of said biologically active substance with said biodegradable polymer are heated at a temperature not lower than the glass transition temperature of said biodegradable polymer but not so high as to cause aggregation of the microcapsules. This method enables the production of very useful sustained release microcapsules adapted to release a bologically active substance at a calculated rate over a protracted time period starting immediately following administration without an initial burst within one day following administration.

14 Claims, No Drawings

METHOD OF PRODUCING SUSTAINED-RELEASE MICROCAPSULES

This application is a division of application Ser. No. 08/562,634, filed Nov. 27, 1995, now U.S. Pat. No. 5,975,987, which is a continuation of application Ser. No. 08/115,149, filed Sep. 2, 1993, now abandoned.

FIELD OF THE INVENTION

The present invention relates to a method of producing sustained-release microcapsules containing a biologically active substance adapted to release said biologically active substance at a constant rate over a protracted time starting immediately following administration without an initial burst.

BACKGROUND OF THE INVENTION

The technology of producing sustained-release microcapsules from a W/O emulsion utilizing a biodegradable polymer is described in, inter alia, JP-A57-118512 and JP-A57-150609.

However, a method of producing sustained-release microcapsules containing a biologically active substance which comprises heating microcapsules at a temperature not lower than the glass transition temperature of the biodegradable polymer but not so high as to cause aggregation of the microcapsules has not been described in the references noted above.

Any sustained-release microcapsule having a biodegradable polymer shell preferably minimizes the initial burst release of the active ingredient to particularly protect against overdosing within one day following administration, and yet adapted to release the active ingredient at a calculated rate over a protracted time period. However, the sustained release-microcapsules heretofore available have the drawback of an initial burst within the day of administration and are, therefore, not fully satisfactory.

SUMMARY OF THE INVENTION

1) According to the present invention, there is provided:
1) A method of producing controlled-release microcapsules containing a biologically active substance from an W/O emulsion comprising an inner aqueous phase containing said biologically active substance and an external oil phase containing a biodegradable polymer, characterized in that microcapsules formed on microencapsulation of said biologically active substance with said biodegradable polymer are heated at a temperature not lower than the glass transition temperature of said biodegradable polymer but not so high as to cause aggregation of the microcapsules; and
2) Sustained-release microcapsules containing a biologically active substance which is produced by heating microcapsules formed on microencapsulation of said biologically active substance with a biodegradable polymer at a temperature not lower than the glass transition temperature of said biodegradable polymer but not so high as to cause aggregation of the microcapsules.

DETAILED DESCRIPTION OF THE INVENTION

The biologically active substance used in the present invention is not specifically limited. Examples thereof include biologically active peptides, antitumor agents, antibiotics, antipyretic/analgestic/antiinflammatory agents, antitussive expectorants, sedatives, muscle relaxants, antiepileptic agents, antiulcer agents, antidepressants, antiallergic agents, cardiotonics, antiarrhythmic agents, vasodilators, hypotensive diuretics, antidiabetic agents, anticoagulants, hemostatics, antituberculous agents, hormone preparations, narcotic antagonists, bone resorption inhibitors and angiogenesis inhibitors and the like.

The biologically active substance to be used in the invention are preferably biologically active peptides. The peptides are preferably those having a molecular weight of about 200 to about 80,000. Examples of the peptides include luteinizing hormone releasing hormone (LH—RH) and its derivatives having like properties, for example the peptides, inclusive of salts thereof, which can be represented by the following formula (I)

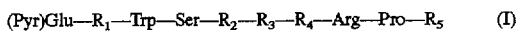

(Pyr)Glu—$R_1$—Trp—Ser—$R_2$—$R_3$—$R_4$—Arg—Pro—$R_5$  (I)

[wherein $R_1$ represents His, Tyr, Trp or p—$NH_2$—Phe; $R_2$ represents Tyr or Phe; $R_3$ represents Gly or a D-amino acid reside; $R_4$ represents Leu, Ile or Nle; $R_5$ represents Gly—NH—$R_6$ (where $R_6$ represents H or a lower alkyl group optionally having a hydroxyl group) or NH—$R_6$ (where $R_6$ is as defined above)] [U.S. Pat. No. 3,853,837, U.S. Pat. No. 4,008,209, U.S. Pat. No. 3,972,859., British Patent 1,423,083, Proceedings of the National Academy of Sciences of the United States of America 78, 6509–6512 (1981)].

Referring to the above formula (I), the D-amino acid residue $R_3$ may, for example, be an α-D-amino acid residue containing up to 9 carbon atoms (e.g. D—Leu, Ile, Nle, Val, Nval, Abu, Phe, Phg, Ser, Thr, Met, Ala, Trp and α-Aibu). These amino acid residues may have been properly protected (with e.g. t-butyl, t-butoxy, t-butoxycarbonyl, etc.). Of course, various acid salts (e.g. carbonates, hydrogen carbonates, acetates, propionates, etc.) and metal complex compounds (e.g. copper complex compounds, zinc complex compounds, etc.) of peptides of general formula (I) can likewise be used.

Where any amino acid or protective group is indicated by an abbreviation in the description of peptides of general formula (I) or those mentioned hereinafter in this specification, the rules of IUPAC-IUB Commission on Biochemical Nomenclature are followed. Furthermore, when any amino acid may occur as optical isomers, the L-compound is meant unless otherwise specified.

As a representative peptide of general formula (I), there may be mentioned the peptide wherein $R_1$=His, $R_2$=Tyr, $R_3$=D—Leu, $R_4$=Leu, $R_5$=$NHCH_2$—$CH_3$ (the acetate of this peptide has the generic name of leuprolerin acetate and will hereinafter be referred to sometimes as TAP-144).

Other examples of biologically active peptides include LH—RH antagonists (cf. U.S. Pat. No. 4,086,219, U.S. Pat. Nos. 4,124,577, 4,253,997 and U.S. Pat. No. 4,317,815).

Further, other examples of biologically active peptides include insulin, somatostatin, somatostatin derivatives (cf. U.S. Pat. Nos. 4,087,390, 4,093,574, 4,100,117, 4,253,998, etc.), growth hormone, prolactin, adrenocorticotropic hormone (ACTH), melanocyte stimulating hormone (MSH), thyrotropin releasing hormone [structural formula (Pyr) Glu—His—$ProNH_2$; briefly TRH] their salts and derivatives (cf. JP-A50-121273 and JP-A52-116465), thyroid stimulating hormone (TSH), luteinizing hormone (LH), follicle stimulating hormone (FSH), vasopressin and its derivatives {cf. Desmopressin [Folia Endocrinologica Japonica, 54: (5), 676–691 (1978)}, oxytocin, calcitonin, parathyroid hormone, glucagon, gastrin, secretin, pancreozymin, cholecystokinin, angiotensin, human placental lactogen, human chorionic gonadotropin (HCG), enkepharin and its derivatives (cf. U.S. Pat. No. 4,277,394, EP-A No. 31567), endorphin, kyotrphin, interferons (e.g. α, β, γ, etc), interleukins (e.g. I, II, III, etc.), tuftsin, thymopoietin, thymosin, thymosthymulin, thymic humoral factor (THF), facteur thymique sérique (FTS) and its derivatives (cf. U.S. Pat. No. 4,229,438), other thymic factors [Advances in Medicine, 125: (10), 835–843 (1983)], tumor necrosis factor (TNF), colony stimulating factor (CSF), motilin, dynorphin, bombesin, neurotensin, caerulein, bradykinin, urokinase, asparaginase, kallikrein, substance P, nerve growth factor, cell growth factor, neurotrophic factor, blood coagulation factors VIII and IX, lysozyme chloride, polymixin B, cholistin, gramicidin, bacitracin, erythropoietin (EPO), peptides having endothelin antagonizing activity (cf. EP-A No. 436189, No. 457195 and No. 496452, JP-A3-94692 and JP-A3-130299) and the like.

Examples of the antitumor agents mentioned above include bleomycin, methotrexate, actinomycin D, mitomycin C, vinblastine sulfate, vincristine sulfate, daunorubicin, adriamycin, neocarzinostatin, cytosine arabinoside, fluorouracil, tetrahydrofuryl-5-fluorouracil, krestin, picibanil, lentinan, levamisole, bestatin, adimexon, glycyrrhizin, Poly I:C, Poly A:U, Poly ICLC and the like.

The above-mentioned antibiotics include, for example, gentamicin, dibekacin, kanendomycin, lividomycin, tobramycin, amikacin, fradiomycin, sisomicin, tetracycline hydrochloride, oxytetracycline hydrochloride, rolitetracycline, doxycycline hydrochloride, ampicillin, piperacillin, ticarcillin, cefalotin, cefaloridine, cefotiam, cefsulodin, cefmenoxime, cefmetazole, cefazolin, cefotaxime, cefoperazone, ceftizoxime, moxalactam, thienamycin, sulfazecin, azthreonam and the like.

Examples of the above-mentioned antipyreticanalgesic-antiinflammatory agents include salicylic acid, sulpyrine, flufenamic acid, diclofenac, indomethacin, morphine, pethidine hydrochloride, levorphanol tartrate, oxymorphone and the like.

Examples of the antitussive expectorants include ephedrine hydrochloride, methylephedrine hydrochloride, noscapine hydrochloride, codeine phosphate, dihydrocodeine phosphate, alloclamide hydrochloride, clofedanol hydrochloride, picoperidamine hydrochloride, cloperastine, protokylol hydrochloride, isoproterenol hydrochloride, salbutamol sulfate, terbutaline sulfate and the like.

Examples of the sedatives include chlorpromazine, prochlorperazine, trifluoperazine, atropine sulfate, methylscopolamine bromide and the like.

Examples of the muscle relaxants include pridinoi methanesulfonate, tubocrarine chloride, pancuronium bromide and the like.

Examples of the antiepileptic agents include phenytoin, ethosuximide, acetazolamide sodium, chlordiazepoxide and the like.

Examples of the antiulcer agents which can be employed include metoclopramide, histidine hydrochloride and the like.

Examples of the antidepressants include imipramine, clomipramine, noxiptiline, phenelzine sulfate and the like.

Examples of the antiallergic agents include diphenhydramine hydrochloride, chlorpheniramine maleate, tripelennamine hydrochloride, methdilazine hydrochloride, clemizole hydrochloride, diphenylpyraline hydrochloride, methoxyphenamine hydrochloride and the like.

Examples of the cardiotonics include trans-π-oxocamphor, teophyllol, aminophylline, etilefrine hydrochloride and the like.

Examples of the antiarrhythmic agents include propranolol, alprenolol, bufetolol, oxyprenolol and the like.

Examples of the vasodilators include oxyphedrine hydrochloride, diltiazem, trazoline hydrochloride, hexobendine, bamethan sulfate and the like.

Examples of the hypotensive diuretics include hexamethonium bromide, pentolinium, mecamylamine hydrochloride, ecarazine hydrochloride, clonidine and the like.

Examples of the antidiabetic agents include glymidine sodium, glipizide, phenformin hydrochloride, buformin hydrochloride, metformin and the like.

Examples of the anticoagulants include heparin sodium, sodium citrate and the like.

Examples of the hemostatics include thromboplastin, thrombin, menadione sodium bisulfite, acetomenaphthone, ε-aminocapric acid, tranexamic acid, carbazochrome sodium sulfonate, adrenochrome monoaminoguanidine methanesulfonate and the like.

Examples of the antituberculotics include isoniazide, ethambutol, paraaminosalicylic acid and the like.

Examples of the hormones preparations include prednisolone, prednisolone sodium phosphate, dexamethasone sodium sulfate, betamethasone sodium phosphate, hexestrol phosphate, hexestrol acetate, methimazole and the like.

Examples of the narcotic antagonists include levallorphan tartrate, nalorphine hydrochloride, naloxone hydrochloride and the like.

Examples of the bone resorption inhibitors include (sulfur-containing alkyl)aminomethylene bisphosphonic acid, and the like.

Examples of the angiogenesis inhibitors include vascularization inhibitory steroids [cf. Science 221: 719 (1983)], fumagillin (cf. EP-A 325119) and fumagillol derivatives (cf. EP-A 357061, 359036, 3866667 and 415294) and the like.

Since an initial burst often occurs with water-soluble species of the above-mentioned drugs, the present invention is more advantageously applied to water-soluble drugs. The water-solubility of the drug is defined by an oil-water partition coefficient between water and n-octanol. The invention is more desirably applied to a drug with an n-octanol/water solubility ratio of not more than 1 and still more desirably to a drug with said ratio of not more than 0.1.

The oil-water partition coefficient can be determined by the method described in Jitsuzaburo Samejima: Buturi Kagaku Jikkenho (Experimental Methodology in Physics and Chemistry), Mokabo, 1961. Thus, a test tube is first filled with n-octanol and buffer (pH 5.5) (1:1). The buffer which can be used includes Sø/rensen buffer [Ergeb. Physiol. 12, 393 (1912)], Clark-Lubs buffer [J. Bact. 2, (1), 109, 191 (1917)], MacIlvaine buffer [J. Biol. Chem. 49, 183 (1921)], Michaelis buffer [Die Wasserstoffionenkonzentration, p. 186 (1914)], Kolthoff buffer [Biochem Z., 179, 410 (1926)] and the like. The tube is then filled with an appropriate amount of the drug, stoppered, and allowed to stand in a constant-temperature bath (25° C.) with intensive shaking from time to time. When the drug has dissolved in the two liquid phases and an equilibrium established, the liquid is allowed to stand or centrifuged and an aliquot of the solution is withdrawn from each layer and analyzed to determine the drug concentration in the layer. Then, the concentration ratio of the drug in the n-octanol layer to that in the water layer is calculated to find the oil-water partition coefficient.

The drug may be as it is or in the form of a pharmacologically acceptable salt thereof (for example, when the drug has a basic group such as amino, salts with inorganic acids such as hydrochloric acid, sulfuric acid and nitric acid, salts with organic acids such as carbonic acid and succinic acid; when the drug has an acidic group such as carboxy, salts with alkali metals such as sodium and potassium, salts with organic bases such as organic amines, e.g. triethylamine, and salts with basic amino acids such as arginine, etc.)

The proper amount of the biologically active substance is dependent on the type of substance, desired pharmacologic effect, duration of action and the like but is generally within the range of about 0.001% to about 90% (w/w) and preferably about 0.01% to about 80% (w/w) based on the shell component biodegradable polymer.

The biodegradable polymer that can be used in the present invention is not limited in kind only if it is sparingly soluble or insoluble in water, biocompatible and degradable in the recipient body. The term 'sparingly soluble' as used here means a solubility of not more than about 3% (w/v) in water.

The biodegradable polymer which can be used include polymers the weight average molecular weights of which are in the range of about 3,000 to about 30,000, preferably about 5,000 to about 25,000, and more preferably about 5,000 to about 20,000. The dispersity of the biodegradable polymer may range from about 1.2 to about 4.0 and preferably from about 1.5 to about 3.5.

It should be understood that the weight average molecular weight values and the polymer dispersity values mentioned in this specification were determined by gel permeation chromatography (GPC).

The proper amount of said biodegradable polymer is dependent on the strength of pharmacologic activity of the biologically active substance used and the desired rate and duration of release of the same substance. As an example, the biodegradable polymer is used as the microcapsule shell in a proportion of about 0.5 to about 10,000 parts by weight, preferably about 1 to about 100 parts by weight, per part by weight of the biologically active substance.

The preferred biodegradable polymer includes, among others, aliphatic polyesters [e.g. homopolymers (e.g. polylactic acid) or copolymers (e.g. lactic acid/glycolic acid copolymer, 2-hydroxybutyric acid/glycolic copolymer) of α-hydroxy acids (e.g. glycolic acid, lactic acid, 2-hydroxybutyric acid, 2-hydroxyvaleric acid, 2-hydroxy-3-methylbutyric acid, 2-hydroxycaproic acid, 2-hydroxyisocaproic acid, 2-hydroxycaprylic acid, etc.), cyclic dimers of α-hydroxy acids (e.g. glycolide, lactide, etc.), hydroxydicarboxylic acids (e.g. malic acid), hydroxytricarboxylic acids (e.g. citric acid), etc., mixtures of such homopolymers and/or copolymers (e.g. a mixture of polylactic acid and 2-hydroxybutyric acid-glycolic acid copolymer)], poly-α-cyanoacrylic esters, polyamino acids (e.g. poly-γ-benzyl-L-glutamic acid, poly-L-alanine, poly-γ-methyl-L-glutamic acid, etc.), maleic anhydride copolymers (e.g. styrene-maleic acid copolymer) and the like. Preferred, among these, are aliphatic polyesters and poly-α-cyanoacrylic esters. The most preferred are aliphatic polyesters.

Further preferred, among such aliphatic polyesters, are the homopolymers and copolymers of α-hydroxy acids or cyclic dimers of α-hydroxy acids and the mixtures of such homopolymers and/or copolymers. The still more preferred are homopolymers or copolymers of α-hydroxy acids, and mixtures of the homopolymers and/or copolymers.

Where any of said α-hydroxy acids, cyclic dimers of α-hydroxy acids, hydroxycarboxylic acids and hydroxytricarboxylic acids has an optical activity center within its molecule, any of its D-, L- and DL-forms can be employed.

The aliphatic polyester can be easily prepared by the known production technology (cf. JP-A61-28521). The mode of polymerization may be random, block or graft.

The weight average molecular weight of said aliphatic polyester is preferably about 3,000 to about 30,000, more preferably about 5,000 to about 25,000, and most preferably about 5,000 to about 20,000. The dispersity of the aliphatic polyester may range preferably from about 1.2 to about 4.0 and most preferably from about 1.5 to about 3.5.

When the aliphatic polyester is a lactic acid-glycolic acid copolymer, its copolymerization ratio is preferably about 100/0 through about 50/50 (by weight). When a 2-hydroxybutyric acid-glycolic acid copolymer is used, its copolymerization ratio is preferably about 100/0 through 25/75 (by weight).

The weight average molecular weight of said lactic acid homopolymer, lactic acid-glycolic copolymer or 2-hydroxybutyric acid-glycolic acid copolymer is preferably about 3,000 to about 30,000, most preferably about 5,000 to about 20,000.

When a mixture of lactic acid homopolymer (A) and glycolic acid-2-hydroxybutyric acid copolymer (B) is used as the aliphatic polyester, the (A)/(B) blend ratio is generally about 10/90 through about 90/10 (by weight) and preferably about 25/75 through about 75/25 (by weight).

The weight average molecular weight of lactic acid homopolymer is preferably about 3,000 to about 30,000, most preferably about 5,000 to about 20,000.

The glycolic acid-2-hydroxybutyric acid copolymer is preferably a copolymer consisting of about 40 to about 70 mole % of glycolic acid and the balance of 2-hydroxybutyric acid. The weight average molecular weight of glycolic acid-2-hydroxybutyric acid copolymer is preferably about 5,000 to about 25,000, most preferably about 5,000 to about 20,000.

Regarding the procedures for producing sustained-release microcapsules containing a biologically active substance from a W/O emulsion comprising an inner aqueous phase containing the biologically active substance and an external oil phase containing a biodegradable polymer in accordance with the present invention, there can be employed any of the known microencapsulation procedures for biologically active substances, such as the drying-in-water method, coacervation method, spray-drying method, and equivalents thereof.

By way of illustration, the biologically active substance is dissolved in water, to begin with, at the final concentration mentioned above, followed, if necessary, by the dissolution or suspension of a drug retaining substance such as gelatin, agar, alginic acid, polyvinyl alcohol, a basic amino acid or the like to provide an inner aqueous phase.

The inner aqueous phase may further contain a pH control agent for insuring the stability and solubility of the biologically active substance. The pH control agent includes carbonic acid, acetic acid, oxalic acid, citric acid, phosphoric acid, hydrochloric acid, sodium hydroxide, and arginine and lysine as well as salts thereof. The inner aqueous phase may also contain a stabilizer for the biologically active peptide, such as albumin, gelatin, citric acid, sodium ethylenediaminetetraacetate, dextrin, sodium hydrosulfite, polyols such as polyethylene glycol, etc., and/or a preservative such as the conventional p-hydroxybenzoic esters (e.g. methylparaben, propylparaben, etc.), benzyl alcohol, chlorobutanol, thimerosal and so on.

The inner aqueous phase prepared in the above manner is poured into said external (oil) phase containing a biodegradable polymer and the mixture is emulsified to provide a W/O emulsion. This emulsification step can be carried out by any of the conventional dispersing procedures such as intermittent agitation, mixing with a propeller or turbine mixer, colloid mill process, homogenizer process or sonication process.

The above-mentioned biodegradable polymer-containing solution (external oil phase) is a solution of the polymer in an organic solvent. The solvent may be any solvent that boils at a temperature not exceeding about 120° C. and is immiscible with water and capable of dissolving the biodegradable polymer. It can, thus, be selected from among halogenated hydrocarbons (e.g. dichloromethane, chloroform, chloroethanol, dichloromethane, trichloroethane, carbon tetrachloride, etc.), fatty acid esters (e.g. ethyl acetate, butyl acetate, etc.), ethers (e.g. ethyl ether, isopropyl ether, etc.), aromatic hydrocarbons (e.g. benzene, toluene, xylene, etc.) and so on. If necessary, two or more different solvents, among them, can be used in an appropriate ratio.

The resulting W/O emulsion is then subjected to microencapsulation.

For the production of microcapsules from the above W/O emulsion by the drying-in-water method, the W/O emulsion is further added to a third aqueous phase to prepare a ternary W/O/W emulsion and the solvent in the oil phase is then evaporated to provide the desired microcapsules.

An emulsifier may be added to the above external aqueous phase. The emulsifier may generally be any substance that is able to form a stable O/W emulsion. Thus, anionic surfactants (e.g. sodium oleate, sodium stearate, sodium lauryl sulfate, etc.), nonionic surfactants (e.g. polyoxyethylene sorbitan fatty acid esters [Tween 80 and Tween 60, Atlas Powder], polyoxy-ethylene-castor oil derivatives [HCO-60 & HCO-50, Nikko Chemicals], etc., polyvinylpyrrolidone, polyvinyl alcohol, carboxymethylcellulose, lecithin, gelatin, etc. can be mentioned. These emulsifiers can be used alone or in combination. The concentration of the emulsifier can be selected within the range of about 0.01% to about 20%, preferably about 0.05% to about 10%.

Evaporation of the solvent from the oil phase can be carried out by any conventional procedure. Thus, while the system is constantly agitated using a propeller mixer or a magnetic stirrer, the solvent may be evaporated at atmospheric pressure or under gradually decreasing pressure or using a rotary evaporator or the like with the degree of vacuum being controlled as required.

The microcapsules thus formed are collected by centrifugation or filtration, rinsed with distilled water several times to remove the excess biologically active peptide, carrier and emulsifier from the surfaces, then redispersed in distilled water or the like and freeze-dried. To prevent aggregation during the washing procedure, an antiaggregation agent [for example, water-soluble polysaccharides such as mannitol, lactose, glucose, starch (e.g. corn starch), etc., amino acids such as glycine, alanine, etc., proteins such as gelatin, fibrin, collagen, etc. and inorganic salts such as sodium chloride, sodium bromide, potassium carbonate, etc.] may be added. The antiaggregation agent is most preferably mannitol. If necessary, the microcapsules are warmed under reduced pressure to further remove the internal water and organic solvent.

For the production of microcapsules by the coacervation method, a coacervating agent is gradually added to said W/O emulsion with stirring to cause separation and solidification of the high polymer.

The coacervating agent is a polymeric substance or a mineral oil- or vegetable oil-based compound, which is miscible with the solvent for the shell component biodegradable polymer but does not dissolve the biodegradable polymer. Thus, for example, silicone oil, sesame oil, soybean oil, corn oil, cottonseed oil, coconut oil, linseed oil, mineral oil, n-hexane, n-heptane, etc. can be mentioned. If desired, these coacervating agents can be used in combination.

The resulting microcapsules are collected by filtration and washed repeatedly with heptane or the like to remove the coacervating agent. Then, in the same manner as in the drying-in-water method, the excess biologically active substance and solvent are removed.

For the production of microcapsules by the spray drying method, said W/O emulsion is sprayed from the nozzle into the drying chamber of a spray drier so that the organic solvent and water within the finely divided liquid droplets may be evaporated in a brief period of time to provide fine microcapsules. The nozzle mentioned above may for example be a two-fluid nozzle, pressure delivery nozzle, rotary disk nozzle or the like. It is also an effective procedure, if necessary for preventing aggregation of microcapsules, to spray an aqueous solution of said antiaggregation agent from another nozzle concurrently with the spray of said W/O emulsion.

The resulting microcapsules may be warmed under reduced pressure, if necessary, to remove water and the solvent from within the microcapsules.

An antiaggregation agent [for example, water-soluble polysaccharides such as mannitol, lactose, glucose, starch (e.g. corn starch), etc., amino acids such as glycine, alanine, etc., proteins such as gelatin, fibrin, collagen, etc. and inorganic salts such as sodium chloride, sodium bromide, potassium carbonate, etc. and so on] may be added to the microcapsules formed on microencapsulation of a biologically active substance with a biodegradable polymer in the present invention The antiaggregation agent is most preferably mannitol.

The particle size of the microcapsules of the invention is dependent on the desired rate of delayed release. When the product is intended for injection, the particle size should satisfy the dispersibility and needle passage requirements. Thus, the mean particle diameter may range from about 1 to about 300 μm and preferably from about 5 to about 150 μm.

The microcapsules thus obtained are heated to a temperature not lower than the glass transition temperature of the shell component biodegradable polymer and not so high as to cause aggregation of the microcapsules. The term 'glass transition temperature' as used herein means the mid-point of the glass transition temperature (Tmg) found with a differential scanning calorimeter (DSC) when a sample is heated at a rate of 10° or 20° C./minute.

As regards the timing of heat treatment, it is preferable that heating be carried out immediately following a drying stage if such a stage is included in the capsule manufacturing process but this is not an exclusive choice. Thus, the heat treatment can be carried out at any time, for example even after withdrawal of the microcapsules from the microencapsulation line.

If the heating temperature is below the glass transition temperature of the shell component biodegradable polymer, the effect of inhibiting the initial burst of the biologically active substance will not be obtained. Conversely, if the temperature is too high, the risk of aggregation and deformation of microcapsules and decomposition or degradation of the biologically active substance will be increased. The heating temperature cannot be specified in general terms but can be determined in consideration of the physical properties (e.g. molecular weight, stability, etc.) of the shell component biodegradable polymer, species of biologically active substance, particle diameter of microcapsules, heating time, degree of desiccation of microcapsules and heating procedure.

As a preferred procedure, the microcapsules are heated at a temperature not below the glass transition temperature of the shell component biodegradable polymer and not so high as to cause aggregation of the microcapsules. For still better results, the micro-capsules are heated at a temperature about 5° C. higher than the glass transition temperature of the biodegradable polymer and not so high as to cause said aggregation. Most preferably, the microcapsules are heated at a temperature about 10° C. higher than the glass transition temperature and not so high as to cause aggregation.

To be specific, the heating temperature is preferably selected from the range from about 5° to about 40° C. higher than the glass transition temperature of the shell component biodegradable polymer. More preferably, the heating temperature is selected from the range from about 5° to about 30° C. higher than the glass transition temperature of the shell component biodegradable polymer. The heating temperature is most preferably selected from the range from about 10° to about 30° C. higher than the glass transition temperature of the biodegradable polymer.

The heating time is also dependent on the heating temperature and the batch size of microcapsules, among other factors. Generally speaking, however, the heating time preferably does not exceed 2 weeks, more preferably is 24 hours or less, after the microcapsules themselves have reached the specified temperature.

The heating method is not critical but any procedure conducive to a uniform heating of microcapsules can be employed.

As specific examples of such procedure, there may be mentioned heating in a constant-temperature bath, a fluidized bed, a moving bed or a kiln, and microwave heating. The most preferred, of them, is heating in a constant-temperature bath.

The microcapsules produced by the method of the invention has a low toxicological potential and can be used safely.

The microcapsules produced by the method of the invention can be administered to the living body in the form of fine granules as produced but can be molded into a variety of dosage forms for administration. They can also be used as a starting material for the manufacture of such pharmaceutical preparations.

Among the pharmaceutical preparations mentioned above are injectable preparations, oral preparations (such as powders, granules, capsules, tablets, etc.), nasal preparations, suppositories (e.g. rectal and vaginal suppositories) and so on. The proper amount of the biologically active substance to be incorporated in such a pharmaceutical preparation varies with the species of physiologically active substance, dosage form, disease to be treated, etc. but is usually about 0.001 mg to about 5 g, preferably about 0.01 mg to about 2 g, per unit dosage form.

These pharmaceutical preparations can be manufactured by the established pharmaceutical technology.

For example, the microcapsules prepared by the method of the invention can be formulated with a dispersing agent [e.g. Tween 80, HCO-60 (Nikko Chemicals), carboxymethylcellulose, sodium alginate, etc.], a preservative (e.g. methylparaben, propylparaben, benzyl alcohol, chlorobutanol, etc.), an isotonizing agent (e.g. sodium chloride, glycerin, sorbitol, glucose, etc.) to provide an aqueous suspension or with a vegetable oil such as olive oil, sesame oil, peanut oil, cottonseed oil, corn oil, propylene glycol or the like to provide an oil suspension for use as an injectable preparation.

Furthermore, the sustained release injectable preparation of said microcapsules may be redispersed with a suspending agent, such as an excipient (e.g. mannitol, sorbitol, lactose, glucose, etc.), and freeze-dried or spray-dried. The resulting solid preparation can be extemporaneously dispersed with distilled water for injection or a suitable dispersion medium to provide a further stabilized sustained release injection.

For the manufacture of pharmaceutical preparations for oral administration, the microcapsules prepared by the method of the invention are formulated with an excipient (e.g. lactose, sucrose, starch, etc.), a disintegrator (e.g. starch, calcium carbonate, etc.), a binder (e.g. starch, gum arabic, carboxymethylcellulose, polyvinylpyrrolidone, hydroxypropylcellulose, etc.) and/or a lubricant (e.g. talc, magnesium stearate, polyethylene glycol 6000, etc.) and the resulting composition is compression-molded in the per se conventional manner. Where necessary, for masking the taste or insuring release in the intestine or an extended duration of action, the moldings can be coated in the per se known manner to provide a desired oral preparation. The coating agent which can be used for this purpose includes, among others, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit (Rhom, Germany; methacrylic acid-acrylic acid copolymer), etc. and pigments such as titanium dioxide and red iron oxide.

For the manufacture of pharmaceutical preparations for nasal administration, the microcapsules prepared by the method of the invention can be processed in the per se known manner to provide a solid, semisolid or liquid preparation. Taking a solid preparation as an example, the microcapsules, either as they are or as formulated with an excipient (e.g. glucose, mannitol, starch, microcrystalline cellulose, etc.), a thickener (e.g. natural gums, cellulose derivatives, acrylic polymers, etc.), can be provided as a powdery composition. The liquid preparation can be manufactured in the form of an oily or aqueous suspension in substantially the same manner as the injectable preparation mentioned above. The semisolid preparation is preferably an aqueous or oleaginous gel or ointment. These preparations may invariably contain a pH control agent (e.g. carbonic acid, phosphoric acid, citric acid, hydrochloric acid, sodium hydroxide) and a preservative (e.g. p-hydroxybenzoic esters, chlorobutanol, benzalkonium chloride). For the manufacture of suppositories, for instance, the microcapsules prepared by the method of the invention can be processed in the per se known manner to provide an oil-based or water-based solid, semisolid or liquid preparation. The oleaginous base which can be used for this purpose is one which does not dissolve the microcapsules and thus includes higher fatty acid triglycerides [e.g. cacao butter, witepsols (Dynamit Nobel)], intermediate fatty acids [e.g. Miglyols (Dynamit Nobel)], and vegetable oils (e.g. sesame oil, soybean oil, cottonseed oil). The aqueous base includes polyethylene glycol, propylene glycol, etc., while the aqueous gel base includes natural gums, cellulose derivatives, vinyl polymers, acrylic polymers and so on.

The microcapsules produced by the method of the present invention are preferably used as an injectable preparation.

The proper dosage of the microcapsules produced by the method of the present invention is dependent on the species and content of biologically active substance, dosage form, scheduled duration of drug release, recipient animal species (e.g. mouse, rat, horse, cattle, man and other warm-blooded mammals) and objective of administration. All that is necessary is that the effective dose of the active substance is contained. For administration to an adult human (body weight 50 kg), the unit dosage of the microcapsules can be selected from the range of about 1 mg to about 10 g, preferably about 10 mg to about 2 g. The dosing volume of the injectable preparation mentioned above can be selected from the range of about 0.1 ml to about 5 ml, preferably about 0.5 ml to about 3 ml.

The biodegradable polymer for use as the shell component of microcapsules can be produced by the methods described in JP-A50-17525, JP-A56-45920, JP-A57-118512, JP-A57-150609, JP-A61-28521, JP-A62-54760, EP-A 481732, or any equivalent thereof.

The following reference and working examples are further descriptive of the present invention. In the following description Tmg means the mid-point of the glass transition temperature described above.

REFERENCE EXAMPLE 1

A 1000 ml four-necked flask equipped with a nitrogen inlet tube and condensor was charged with 495.4 g of a 90% (w/w) aqueous solution of D,L-lactic acid and the charge was heated in a nitrogen gas stream under reduced pressure from 90° C./400 mmHg to 150° C./30 mmHg over a period of 5 hours, with the distillate water being constantly removed. The reaction mixture was further heated under reduced pressure at 5–7 mmHg/150°–175° C. for 65 hours, after which it was cooled to provide an amber-colored polylactic acid.

This polymer was dissolved in 1000 ml of dichloromethane and the solution was poured in warm water at 60° C. with stirring. The resulting pasty polymeric precipitate was collected and dried in vacuo at 30° C.

The peak molecular weight value of the above lactic acid polymer as determined by GPC was 16,000 and the Tmg value of the same polymer in DSC was 40° C.

REFERENCE EXAMPLE 2

A 1000 ml four-necked flask equipped with a nitrogen inlet tube and condensor was charged with 247.7 g of a 90% (w/w) aqueous solution of D,L-lactic acid and 190.2 g of glycolic acid and the charge was heated in a nitrogen gas stream under reduced pressure from 90° C./500 mmHg to 150° C./30 mmHg for a period of 5 hours, with the distillate water being constantly removed. The reaction mixture was further heated under reduced pressure at 5–7 mmHg/ 150°–180° C. for 28 hours, after which it was cooled to provide an amber-colored lactic acid-glycolic acid copolymer. [lactic acid/glycoic acid: 50/50 (mole/mole %)]

This copolymer was dissolved in 1000 ml of dichloromethane and the solution was poured in warm water at 60° C. with stirring. The resulting pasty polymeric precipitate was collected and dried in vacuo at 30° C.

The peak molecular weight value of the above lactic acid-glycolic acid copolymer as determined by GPC was 12,000 and the Tmg value of the same copolymer in DSC was 36° C.

REFERENCE EXAMPLE 3

A 1000 ml four-necked flask equipped with a nitrogen inlet tube and condensor was charged with 145.8 g of D,L-2-hydroxybutyric acid and 177.7 g of glycolic acid and the charge was heated in a nitrogen gas stream under reduced pressure from 100° C./500 mmHg to 150° C./30 mmHg for a period of 3.5 hours, with the distillate water being constantly removed. The reaction mixture was further heated under reduced pressure at 5–7 mmHg/150°–180° C. for 27 hours, after which it was cooled to provide an amber-colored 2-hydroxybutyric acid-glycolic acid copolymer. [2-hydroxybutyric acid/glycolic acid: 37.5/62.5 (mole/mole %)]

This copolymer was dissolved in 1000 ml of dichloromethane and the solution was poured in warm water at 60° C. with stirring. The resulting pasty polymeric precipitate was collected and dried in vacuo at 25° C.

The peak molecular weight value of the above 2-hydroxybutyric acid-glycolic acid copolymer as determined by GPC was 14,000 and the Tmg value of the same copolymer in DSC was 26° C.

REFERENCE EXAMPLE 4

A 1000 ml four-necked flask equipped with a nitrogen inlet tube and condensor was charged with 300 g of a 90% (w/w) aqueous solution of D,L-lactic acid and 100 g of a 90% (w/w) aqueous solution of L-lactic acid and the charge was heated in a nitrogen gas stream under reduced pressure from 100° C./500 mmHg to 150° C./30 mmHg for a period of 4 hours, with the distillate water being constantly removed. The reaction mixture was further heated under reduced pressure at 5–7 mmHg/150°–180° C. for 24 hours, after which it was cooled to provide an amber-colored polylactic acid.

This polymer Was dissolved in 1000 ml of dichloromethane and the solution was poured in warm water at 60° C. with stirring. The resulting pasty polymeric precipitate was collected and dried in vacuo at 30° C.

The peak molecular weight value of the above polylactic acid as determined by GPC was 7,000 and the Tmg value of the same copolymer in DSC was 33° C.

REFERENCE EXAMPLE 5

In 0.5 ml of distilled water was dissolved (Pyr)—Glu—His—Trp—Ser—Tyr—D—Leu—Leu—Arg—Pro—NH—$C_2H_5$ and the solution was added to a solution of polylactic acid (4.0 g), obtained in Reference Example 1, in 7.5 ml of dichloromethane. The mixture was homogenized on a compact homogenizer for 60 seconds to provide a W/O emulsion. After cooling to 17° C., this emulsion was poured in 1000 ml of 0.1% (w/v) aqueous polyvinyl alcohol and the mixture was homogenized using a turbine homomixer to provide a W/O/W emulsion. This W/O/W emulsion was stirred at room temperature to evaporate the dichloromethane and, thereby, solidify the internal W/O emulsion, after which the microcapsules were collected by centrifugation. These microcapsules were redispersed in distilled water and further centrifuged to wash off the excess drug and other reagents. To the recovered microcapsules was added 0.3 g of D-mannitol and the mixture was freeze-dried to provide a powdery lyophilizate.

REFERENCE EXAMPLE 6

The microcapsules obtained as a powder in Reference Example 5 were heated in a constant-temperature bath at 90° C., viz. a temperature 50° C. higher than Tmg of the shell component polylactic acid, for 2 hours. An attempt was then made to subject the microcapsules to an in vitro release test in the manner described in Example 1 which appears hereinafter. However, the microcapsules had been fused together so that they could not be dispersed in phosphate buffer at pH 7.0.

REFERENCE EXAMPLE 7

In 0.4 ml of distilled water was dissolved 400 mg of (Pyr)—Glu—His—Trp—Ser—Tyr—D—Leu—Leu—Arg—Pro—NH—$C_2H_5$ and the solution was added to a solution of lactic acid-glycolic acid copolymer [lactic acid/glycolic acid: 50/50 (mole/mole %)] (4.0 g), prepared in Reference Example 2, in 5.0 ml of dichloromethane. The mixture was homogenized on a compact homogenizer for 60 seconds to provide a W/O emulsion. Using this emulsion, microcapsules were prepared as in Reference Example 5.

REFERENCE EXAMPLE 8

In 0.2 ml of distilled water was dissolved 500 mg of thyroid hormone releasing hormone (TRH) and the solution was added to a solution of lactic acid-glycolic acid copolymer [lactic acid/glycolic acid: 50/50 (mole/mole %)] (4.5 g), prepared in Reference Example 2, in 4.7 ml of dichloromethane. The mixture was homogenized on a compact homogenizer for 60 seconds to provide a W/O emulsion. Using this emulsion, microcapsules were prepared as in Reference Example 5.

REFERENCE EXAMPLE 9

In 0.4 ml of distilled water was dissolved 400 mg of (Pyr)—Glu—His—Trp—Ser—Tyr—D—Leu—Leu—Arg—Pro—NH—$C_2H_5$ and the solution was added to a 1:1 (w/w) solution of 2-hydroxybutyric acid-glycolic acid copolymer, obtained in Reference Example 3, and polylactic acid, obtained in Reference Example 4, in 5.0 ml of dichloromethane. The mixture was homogenized on a compact homogenizer for 60 seconds to provide a W/O emulsion. Using this emulsion, microcapsules were prepared as in Reference Example 5.

EXAMPLE 1

The microcapsules obtained as a powder in Reference Example 5 were heated in a constant-temperature bath at 45° C., viz. a temperature 5° C. higher than Tmg of the shell component polylactic acid, for 2 weeks. The resulting microcapsules were subjected to an in vitro release test in phosphate buffer (pH 7.0) at 37° C. and 120 cycles/minute. The drug release rate found after one day is shown in Table 1.

EXAMPLE 2

The microcapsules obtained as a powder in Reference Example 5 were heated in a constant-temperature bath at 60° C., viz. a temperature 20° C. higher than Tmg of the shell component polylactic acid, for 4 hours. The resulting microcapsules were subjected to an in vitro release test as in Example 1. The one-day drug release rate thus found is shown in Table 1.

TABLE 1

| One-day drug release rate (%) | |
|---|---|
| Example 1 | 13.2 ± 0.4 |
| Example 2 | 6.0 ± 0.2 |

EXAMPLE 3

The microcapsules obtained as a powder in Reference Example 7 were heated in a constant-temperature bath at 56° C., viz. a temperature 20° C. higher than Tmg of the shell component lactic acid-glycolic acid copolymer, for 1 hour. The resulting microcapsules were subjected to an in vitro release test as in Example 1. The one-day drug release rate thus found is shown in Table 2.

EXAMPLE 4

The microcapsules obtained as a powder in Reference Example 7 were heated in a constant-temperature bath at 56° C., viz. a temperature 20° C. higher than Tmg of the shell component lactic acid-glycolic acid copolymer, for 5 hours. The resulting microcapsules were subjected to an in vitro release test as in Example 1. The one-day drug release rate thus found is shown in Table 2.

TABLE 2

| One-day drug release rate (%) | |
|---|---|
| Example 3 | 12.7 ± 0.4 |
| Example 4 | 7.8 ± 0.6 |

EXAMPLE 5

The microcapsules obtained as a powder in Reference Example 8 were heated in a constant-temperature bath at 56° C., viz. a temperature 20° C. higher than Tmg of the shell component lactic acid-glycolic acid copolymer, for 4 hours. The resulting microcapsules were subjected to an in vitro release test as in Example 1. The one-day drug release rate thus found is shown in Table 3. Further the drug release rate in the case of no heat-treatment is shown as a control.

TABLE 3

| One-day drug release rate (%) | |
|---|---|
| Control | 9.0 ± 0.4 |
| Example 5 | 4.9 ± 0.1 |

EXAMPLE 6

The microcapsules obtained as a powder in Reference Example 9 were heat-treated in a constant temperature bath at 55° C., viz. a temperature 24° C. higher than Tmg (31° C.) of a 1:1 (w/w) mixture of 2-hydroxybutyric acid-glycolic acid copolymer, for 8 hours and, then, subjected to an in vitro release test under the same conditions as described in Example 1. The one-day drug release rate thus found is shown in Table 4.

EXAMPLE 7

The microcapsules obtained as a powder in Reference Example 9 were heat-treated in a constant temperature bath at 50° C., a temperature 19° C. higher than Tmg (31° C.) of a 1:1 (w/w) mixture of 2-hydroxybutyric acid-glycolic acid copolymer for 1 week and, then, subjected to an in vitro release test under the same conditions as described in Example 1. The one-day drug release rate thus found is shown in Table 4.

TABLE 4

| One-day drug release rate (%) | |
| --- | --- |
| Example 6 | 5.7 ± 0.2 |
| Example 7 | 6.2 ± 0.1 |

EXAMPLE 8

The microcapsules obtained in Example 1 were administered subcutaneously to rats (n=5) and the residual amount of the drug was determined. The one-day release rate thus found is shown in Table 5.

TABLE 5

| One-day drug release rate (%) | |
| --- | --- |
| Example 8 | 12.1 ± 0.5 |

EXAMPLE 9

In 0.5 ml of distilled water were dissolved interferon α (IFN-α) (60 mg) and human serum albumin (200 mg). The resulting solution was added to a solution of lactic acid-glycolic acid copolymer [lactic acid/glycolic acid: 50/50 (mole/mole %), weight average molecular weight: 6,400, Tmg in DSC: 30° C. Wako] (1.74 g) in 2.0 ml of dichloromethane. The mixture was homogenized on a compact homogenizer for 20 seconds to provide a W/O emulsion. Microcapsules were prepared in the same manner described in Reference Example 5 except that D-mannitol was not added. After addition of 87 mg of D-mannitol to the microcapsules (75 mg), the mixture (microcapsules and D-mannitol) was heated at 50° C., viz. a temperature 20° C. higher than Tmg of the shell component lactic acid-glycolic acid copolymer, for 16 hours. The microcapsules thus obtained were administered subcutaneously to rats (n=4) and the blood-level of IFN-α 1 hour after administration is shown in Table 6. The blood-level of IFN-α in the case of no heat-treatment is shown as a control. Injected amounts of microcapsules were 10 mg in each case.

TABLE 6

| Blood-level of IFN-α 1 hour after administration (IU/ml) | |
| --- | --- |
| Control | 1011 ± 209 |
| Example 9 | 307 ± 85 |

The method of the invention enables the production of very useful sustained release microcapsules adapted to release a biologically active substance at a calculated rate over a protracted time period starting immediately following administration without an initial burst within one day following administration.

What is claimed is:

1. A method of producing sustained-release microcapsules containing a biologically active substance from an W/O emulsion comprising an inner aqueous phase containing said biologically active substance and an external oil phase containing a biodegradable polymer, characterized in that microcapsules formed on microencapsulation of said biologically active substance with said biodegradable polymer are heated at a temperature not lower than the glass transition temperature of said biodegradable polymer but not so high as to cause aggregation of the microcapsules.

2. The method according to claim 1 wherein the biologically active substance is a peptide having a molecular weight of about 200 to 80,000.

3. The method according to claim 1 wherein the biologically active substance is luteinizing hormone releasing hormone or its derivatives.

4. The method according to claim 1 wherein the biodegradable polymer is an aliphatic polyester.

5. The method according to claim 4 wherein the aliphatic polyester is a homopolymer or copolymer of α-hydroxy acids, or a mixture of the homopolymer and/or copolymer.

6. The method according to claim 4 wherein the weight average molecular weight of the aliphatic ester is about 3,000 to 30,000.

7. The method according to claim 4 wherein the dispersity of the aliphatic ester is about 1.2 to 4.0.

8. The method according to claim 1 wherein the microcapsules are heated at a temperature of about 5° to 40° C. higher than the glass transition temperature of the biodegradable polymer.

9. The method according to claim 1 wherein the mean particle diameter ranges from about 1 to 300 μm.

10. The method according to claim 1 wherein a heating is carried out after an antiaggregation agent is added to the microcapsules formed on microencapsulation.

11. Sustained-release microcapsules containing a biologically active substance which is produced by heating microcapsules formed on microencapsulation of said biologically active substance with a biodegradable polymer at a temperature not lower than the glass transition temperature of said biodegradable polymer but not so high as to cause aggregation of the microcapsules.

12. The sustained-release microcapsules containing a biologically active substance according to claim 11 wherein an antiaggregation agent is added to the microcapsules formed on microencapsulation.

13. An injectable preparation comprising sustained-release microcapsules containing a biologically active substance according to claim 11.

14. A method of producing sustained-release microcapsules containing a biologically active substance from an W/O emulsion comprising an inner aqueous phase containing said biologically active substance and an external oil phase containing a biodegradable polymer, wherein microcapsules formed on microencapsulation of said biologically active substance with said biodegradable polymer are heated at a temperature between that which not lower than the glass transition temperature of said biodegradable polymer and a temperature 40° C. higher than said the glass transition temperature.

* * * * *